United States Patent [19]

Hedges et al.

[11] Patent Number: 4,620,950

[45] Date of Patent: Nov. 4, 1986

[54] PROCESS FOR PREPARING ARYL SULFONE SULFONIC ACIDS

[75] Inventors: Charles V. Hedges, Mt. Vernon; Victor Mark, Evansville, both of Ind.

[73] Assignee: General Electric Company, Mt. Vernon, Ind.

[21] Appl. No.: 301,396

[22] Filed: Sep. 11, 1981

Related U.S. Application Data

[63] Continuation of Ser. No. 154,837, May 30, 1980, abandoned, which is a continuation of Ser. No. 745,638, Nov. 29, 1976, abandoned.

[51] Int. Cl.$^4$ ............................................. C07C 143/24
[52] U.S. Cl. ................................................. 260/505 R
[58] Field of Search ......... 260/505 C, 505 B, 607 AR

[56] References Cited

U.S. PATENT DOCUMENTS 2,010,754  8/1935  Felix et al. ................... 260/607 AR
3,948,851  4/1976  Mark .

FOREIGN PATENT DOCUMENTS 820659  4/1958  United Kingdom .

OTHER PUBLICATIONS

Everett E. Gilbert—*Sulfonation and Related Reactions* 1965—pp. 4–6, 15–18, 62–92 and 108.

*Primary Examiner*—Alan Siegel
*Attorney, Agent, or Firm*—Martin B. Barancik

[57] ABSTRACT

A process for preparing aryl sulfone sulfonic acids by reacting an aryl sulfone in the molten state with sulfur trioxide under substantially anhydrous conditions.

3 Claims, No Drawings

PROCESS FOR PREPARING ARYL SULFONE SULFONIC ACIDS

This is a continuation of application Ser. No. 154,837, filed 5/30/80, now abandoned, which is a continuation of application Ser. No. 745,638 filed 11/29/76, now abandoned.

This invention is directed to a process for preparing aryl sulfone sulfonic acids by reacting aryl sulfone in the molten state with sulfur trioxide under substantially anhydrous conditions.

BACKGROUND OF THE INVENTION

Aryl sulfone sulfonic acids are useful as leveling agents for certain nylons and as starting materials for a variety of additives especially flame-retardant additives for polymer systems. The aryl sulfone sulfonic acids have been previously prepared by several different methods as, for example, by the reaction of a phenylsulfone and chlorosulfonic acid or oleum.

Both of these methods, however, have serious drawbacks. When using chlorosulfonic acid, the primary product is the sulfonyl chloride that has to be converted to the acid by an additional hydrolysis step. This has the disadvantage, not only of requiring additional reagents and an extra reaction step, but it also requires the disposition of the co-product, hydrochloric acid. Sulfonation by oleum has, of course, the disadvantage of employing large amounts of sulfuric acid, which not only have to be separated from the desired sulfonic acid product, but also have to be disposed of in an ecologically acceptable manner. While these drawbacks of these two sulfonating reagents points to the use of liquid $SO_3$ as the desirable reagent, the prior art of sulfonation, as exemplified by Evert Gilbert, "Sulfonation and Related Reactions", Interscience publishers, (1965), requires the use of compatible solvents.

The discovery has been made that under carefully controlled conditions, molten aryl sulfone, specifically diphenylsulfone, can be sulfonated directly in the absence of solvent by liquid $SO_3$ with the formation of only trace amounts of sulfuric acid. The small amounts of the latter by-product can be quantitatively separated from the arylsulfone sulfonic acids by the use of stoichiometric amounts of barium hydroxide, for example. Furthermore, and surprisingly, carefully controlled conditions can also lead to diaryl sulfone disulfonic acids, again with minimum amounts of by-product sulfuric acid formation. The avoidance of solvents, few of which are chemically compatible with liquid $SO_3$, not only results in the formation of better product but also leads to economical processes.

DESCRIPTION OF THE INVENTION

The present invention is directed to a process for preparing aryl sulfone sulfonic acids by reacting an aryl sulfone in the molten state with sulfur trioxide under substantially anhydrous conditions.

The aryl sulfone starting materials are of the following formula:

$$R-SO_2-R_1$$

wherein R and $R_1$ are independently selected from $C_1$-$C_{15}$ alkyl, aryl of 6 to 14 carbon atoms, or substituted aryl wherein the substituents are selected from halogen (Cl, Br, F), $C_1$-$C_{15}$ alkyl, $C_1$-$C_{15}$ alkoxy, aryloxy of 6 to 14 carbon atoms, arylthio of 6 to 14 carbon atoms, nitro, or trifluoromethyl, with the proviso that one of R or $R_1$ is aryl or substituted aryl.

The preferred aryl sulfones include diphenyl sulfone, di(p-tolyl)sulfone; phenyl 4-chlorophenyl sulfone; 4,4'-dibromodiphenyl sulfone; 4-chloro-4'-nitrodiphenyl sulfone; 4-chloro-3'-(trifluoromethyl)diphenyl sulfone; 4,4'-dichlorodiphenyl sulfone; 4,2',4',5'-tetrachlorodiphenyl sulfone; 4,4'-dichloro-1,1-dinaphthyl sulfone; methyl phenyl sulfone; benzyl phenyl sulfone.

The nature of sulfur trioxide used in the process, according to the invention, is not critical and it is possible to use either the liquid stabilized gamma modification of sulfur trioxide, or even a gaseous mixture containing gaseous sulfur trioxide, such as obtained in the conversion of $SO_2$ into $SO_3$ by oxidation with air.

The aryl sulfone will determine the reaction temperature since the reaction is carried at or above the melting point of the aryl sulfone. The absence of solvents in the instant process allows the use of a wider temperature range in the process, since it is not limited by the boiling point of any solvent. The instant temperature range may encompass temperatures of 25° C. to about 200° C. Preferably, this temperature range encompasses compounds which melt between 50° C. and about 150° C.

Since the sulfonation reaction is exothermic, proper cooling may be required to maintain the reaction within the desired temperature range. Conversely, the rate of introduction of sulfur trioxide may be conducted such that the desired reaction temperature is maintained.

Pressure is not critical, thus the instant reaction can be conducted at atmospheric or superatmospheric pressures.

The ratio of $SO_3$ to aryl sulfone is determined by whether mono-, di-, or polysulfonation is desired. Since the reaction of aryl sulfone is quantitative, stoichiometric or slight excess of $SO_3$ is used. When anhydrous conditions are maintained, no by-product sulfuric acid is formed and also, by-product sulfone formation is minimized.

Since at the proper temperature the reaction is almost instantaneous, very short reaction times are feasible, and reaction cycles of one or a few hours are thus obtainable.

The workup of the reaction product mixture is best carried out with the use of water, since the sulfonic acid products, but not the starting materials, are water soluble. Simple filtration, for example, allows separation of the water soluble sulfonic acid and water insoluble starting materials. Subsequent workup is determined by the nature of desired product. If, for instance, the neutral alkali or alkaline earth metal salts of the sulfonic acids are desired, the aqueous phase is simply neutralized by the proper base, and the water removed either by distillation or drying or, if the salt is insoluble, then by filtration. If a sulfuric acid-free product is desired, stoichiometric amounts of barium hydroxide are added, which quantitatively precipitates the sulfuric acid as barium sulfate and this is removable by filtration, leaving behind the sulfuric acid-free sulfonic acid product.

PREFERRED EMBODIMENT OF THE DESCRIPTION

The following non-limiting examples illustrate the process of this invention.

EXAMPLE 1

In a 1 liter, 4-necked flask, equipped with Teflon stirrer, reflux condenser, 100 ml addition funnel and thermometer dipping into the reaction mixture, is charged 218.3 g. (1.0 mole) of pure diphenyl sulfone and heated to its melting point of 125°–127° C. with the aid of a heating mantel. When all of the sulfone is melted, 128.0 g. (1.6 mole) of stabilised, liquid sulfur trioxide is added gradually, while maintaining the temperature of the reaction mixture between 120° C. and 130° C. by regulating the rates of addition of sulfur trioxide and external heating or cooling. The addition requires about 20–30 minutes, after which heating is continued for an additional 30-minute period within the above temperature range. The resultant melt is added to 650 ml of cold water, whereby a white slurry results, which is stirred and filtered, after it is cooled to 25° C., through a sintered glass funnel by suction, the filtercake is washed twice with 100 ml portions of water and dried. Its dry weight of 9.17 g. indicates that 95.8% of the sulfone was converted into sulfonic acids. The clear, aqueous filtrate, 1180 g., was analyzed for sulfuric acid content and for the ratio of mono- and disulfonic acids.

Determination of sulfuric acid in the aqueous phase by amperometric titration using lead nitrate as precipitating agent indicated its presence as 0.96% or 11.3 g. or 0.115 mole of sulfuric acid, or 7.2% based on the amount of $SO_3$ employed. The mono- to disulfonic acid ratio was determined by neutralizing an aliquot of the acid solution by potassium hydroxide, evaporation of water, determining the dry weight of the salt mixture and defining its composition by reverse phase liquid chromatography using water-methanol mixture as diluant. The dry weight of the neutralized aliquot was equivalent to 381.1 g. of potasssium salt of the sulfonic mixture, which was found to consist of 47.6% of potassium diphenyl sulfone-3-sulfonate and 52.4% of dipotassium diphenyl sulfone-3,3'-disulfonate. These data indicate that in the sulfonation of one mole of molten diphenyl sulfone by 1.6 mole of liquid $SO_3$, 0.53 mole of mono- and 0.43 mole of disulfonic acids were formed, giving a 96% yield based on the sulfone.

EXAMPLE 2

The procedure of Example 1 was exactly repeated, except that gaseous instead of liquid $SO_3$ was employed. There was no significant difference either in yield or in product composition.

EXAMPLE 3

The procedure of Example 1 was repeated except that 4-chlorodiphenyl sulfone was used instead of diphenyl sulfone. An over 90% yield of sulfonated products were obtained comprising 76% of 4-chlorodiphenyl sulfone-3'-sulfonic acid and 24% of 4-chlorodiphenyl sulfone-3,3'-disulfonic acid.

EXAMPLE 4

The procedure of Example 1 was repeated except that methyl phenyl sulfone was used instead of diphenyl sulfone. A 92% yield of methyl phenyl sulfone-3-sulfonic acid was obtained and identified by nmr, ir and liquid chromatography retention time. No disulfonic acid was detectable.

EXAMPLE 5

The procedure of Example 1 was repeated using 4,2',4',5'-tetrachlorodiphenyl sulfone in place of diphenyl sulfone. An 87% yield of 4,2',4',5'-tetrachlorodiphenyl sulfone-3-sulfonic acid was obtained.

EXAMPLE 6

The advantages of the instant method over the conventional sulfonation technique using oleum is herein illustrated whereby oleum is used as the sulfonating agent.

Employing 266.8 g. of 30% oleum for one mole of diphenyl sulfone and carrying out the reaction as described in Example 1, there was recovered 31.6 g. of unreacted sulfone, indicating a maximum yield of only 85% of the theoretical. In addition to the diphenyl sulfonesulfonic acids produced, the reaction mixture also contained 201 g. of sulfuric acid, comprising both introduced and generated sulfuric acid. This required enormous amounts of barium or calcium hydroxide to yield a sulfuric acid-free product.

EXAMPLE 7

To further illustrate the advantage of the instant method over a conventional method using solvents, the sulfonation of diphenyl sulfone was carried out in 1,2-dichloroethane solution at 70° C. By employing even a 2:1 mole ratio of $SO_3$ to diphenyl sulfone, there was realized a maximum of only 80% conversion to sulfonic acids, consisting of 1.7 to 1.0 weight ratio of mono- to disulfonic acid of diphenyl sulfone. Emulsion formation plus the relatively large amounts of solvent required are additional disadvantages of the process.

Obviously, other modifications and variations of the present invention are possible in the light of the above teachings. It is, therefore, to be understood that changes may be made in the particular embodiment described which will be within the full intended scope of the invention as defined by the appended claims.

What is claimed:

1. A process for sulfonating diphenyl sulfone which comprises contacting diphenyl sulfone in its molten state with a sulfonating agent consisting essentially of sulfur trioxide under substantially anhydrous conditions in the absence of a solvent.

2. A process in accordance with claim 1 wherein the sulfur trioxide is liquid.

3. A process in accordance with claim 1 wherein the sulfur trioxide is gaseous.

* * * * *